United States Patent [19]
Braswell et al.

[11] Patent Number: 5,911,992
[45] Date of Patent: Jun. 15, 1999

[54] METHOD FOR CONTROLLING WEIGHT WITH HYPERICUM PERFORATUM AND GARCINIA CAMBOGIA

[75] Inventors: A. Glenn Braswell, Atlanta, Ga.; Aftab J. Ahmed, Marina Del Ray, Calif.

[73] Assignee: A. Glenn Braswell, Atlanta, Ga.

[21] Appl. No.: 08/874,033

[22] Filed: Jun. 12, 1997

[51] Int. Cl.⁶ .......................... A61K 35/78; A61K 35/42; C07C 59/265; C07C 35/16
[52] U.S. Cl. ...................... 424/195.1; 514/909; 514/910; 514/557; 562/584; 568/833
[58] Field of Search ........................ 424/195.1; 514/909, 514/557, 910; 562/584; 568/833

[56] References Cited

U.S. PATENT DOCUMENTS

| | | | |
|---|---|---|---|
| 5,273,754 | 12/1993 | Mann | 424/440 |
| 5,612,039 | 3/1997 | Policappelli et al. | 424/195.1 |

FOREIGN PATENT DOCUMENTS

| | | |
|---|---|---|
| 0 599 307 | 6/1994 | European Pat. Off. |
| 0 803 202 A2 | 10/1997 | European Pat. Off. |
| 9-51779 | 2/1997 | Japan . |
| WO 93 08186 | 4/1993 | WIPO . |

OTHER PUBLICATIONS

Ayuga Tellez et al., "Study of the Anorexic Effect of Hypericum–caprifolium Boiss", vol. 54, No. 2, 1988, pp. 320–324.
Davis et al., "Advances and Retreats in the Pharmacotherapy of Obesity", vol. 141, No. 23, Dec. 8, 1997, pp. 141–121. Aspects, Ed. L.J. Machlin, Marcel Dekker, Inc., pp. 329 and 363, 1984.
Wurtman et al., "Brain Serotonin, Carbohydrate–Craving, Obesity and Depression," *Obesity Research,* vol. 3, Supp. 4, pp. 477S–480S (1995).
Murray, *The Healing Power of Herbs,* 2nd Edition, pp. 294–301 (1995).
Castleman, *The Healing Herbs,* pp. 321–325 (1991).
Harrer et al., "Treatment of Mild/Moderate Depressions with Hypericum," *Phytomedicine,* vol. 1, pp. 3–8 (1994).
De Smet et al., "St. John's Wort as an Antidepressant," *BMJ London,* Aug. 3, 1996.
Perovic et al., "Pharmacological Profile of Hypericum Extract," *Drug Research,* vol. 45 (II), No. 11, pp. 1145–1148 (1995).
Sullivan et al., "Mechanisms of Appetite Modulation by Drugs," *Federation Proceedings,* vol. 44, No. 1, part 1, pp. 139–144 (1985).
Stone, "Lipid Management: Current Diet Drug Treatment Options," *The American Journal of Medicine,* vol. 101, supp. 4A, pp. 40S–49S (1996).
Watson et al., "Citrate and the Conversion of Carbohydrate into Fat," *The Journal of Biological Chemistry,* vol. 245, No. 22, pp. 5993–6002 (1970).
Rao et al, "Lipid–Lowering and Antiobesity Effect of (–)Hydroxycitric Acid," *Nutrition Research,* vol. 8, pp. 209–212 (1988).
Hellerstein et al., "The Indirect Pathway of Hepatic Glycogen Synthesis and Reduction of Food Intake by Metabolic Inhibitors," *Life Sciences,* vol. 53, pp. 1833–1845 (1993).
Sullivan et al., "Factors Influencing in the in vitro Rates of Lipogenesis in Rat Liver," *J. Nutrition,* vol. 101, pp. 265–272 (1971).
A New Way to Battle the Bulge—advertisement. *Journal of Longevity Research,* vol. 3, No. 3, Mar. 1997, p. 29.
Sullivan et al., "Metabolic Regulation as a Control for Lipid Disorders. (II). Influence of (–)-Hydroxycitrate on Genetically and Experimentally Induced Hypertriglyceridema in the Rat," *The American Journal of Clinical Nutrition,* vol. 30, May 1977, pp. 777–784.
Sullivan et al., "Effect of (–)-Hydroxycitrate upon the Accumulation of Lipid in the Rat: I. Lipogenesis," *Lipids,* vol. 9, No. 2, pp. 121–128.
Sullivan et al., "Metabolic Regulation as a Control for Lipid Disorders. I. Influence of (–)-Hydroxycitrate on Experimentally Induced Obesity in the Rodent," *The American Journal of Clinical Nutrition,* vol. 30, May 1977, pp. 767–776.
Sergio, "A Natural Food, The Malabar Tamarind, May be Effective in the Treatment of Obesity," *Medical Hypotheses,* vol. 27, pp. 39–40 (1988).
Lowenstein, "Effect of (–)-Hydroxycitrate on Fatty Acid Synthesis by Rat Liver in Vivo," *The Journal of Biological Chemistry,* vol. 344, No. 2, Feb. 10, 1971, pp. 629–632.
Lewis et al., (–)-Hydroxycitric Acid—The Principal Acid in the Fruits of *Garcinia Cambogia*Desr., *Phytochemistry,* vol. 4, 1965, pp. 619–625.
Melzer et al., "Vasoactive Properties of Procyanidins from Hypericum perforatum L. In Isolated Porcine Coronary Arteries," *Drug Research,* vol. 14, No. 5 (1991), pp. 481–483.
Thiede et al., "Inhibition of MAO and COMT by Hypericum Extracts and Hypercin," Journal of Geriatric Psychiatry and Neurology, vol. 7, supp. 1, Oct. 1994.

(List continued on next page.)

*Primary Examiner*—David M. Naff
*Assistant Examiner*—Janet M. Kerr
*Attorney, Agent, or Firm*—Arter & Hadden, LLP

[57] ABSTRACT

A method of controlling weight in mammals by orally administering to the mammal an amount of a pharmaceutical composition containing *Hypericum perforatum* or active components thereof effective to control the weight of the mammal is described. The pharmaceutical composition also preferably further contains at least one thermogenic agent and at least one agent inhibiting lipogenesis. The at least one thermogenic agent includes one or more of N-acetyl-L-carnitine, cayenne extract, inositol hexanicotinate, niacin or salicin. The at least one agent inhibiting lipogenesis may be hydroxy citric acid. When the pharmaceutical composition includes *Hypericum perforatum*, at least one thermogenic agent and at least one agent inhibiting lipogenesis, the composition acts to control the weight of the mammal by simultaneously suppressing appetite, inducing thermogenesis and inhibiting lipogenesis.

16 Claims, No Drawings

OTHER PUBLICATIONS

Suzuki et al, "Inhibition of Monoamine Oxidase by Hypericin," *Planta Medica,* 1984, pp. 272–273.

"Pyridoxine (Vitamin $B^6$)," pp. 100–110.

Casacchia et al., "Pyridoxine and Depression: Neuroendocrine Aspects," pp. 55–58.

Dudman et al., "Disordered Methionine/Homocysteine Metabolism in Premature Vascular Disease," Arteriosclerosis and Thrombosis, vol. 13, No. 9, Sep. 1933, pp. 1253–1260.

Aldermann et al., "Effect of a Modified, Well–Tolerated Niacin Regimen on Serum Total Cholesterol, High Density Lipoprotein Cholesterol and the Cholesterol to High Density Lipoprotein Ratio," *The American Journal of Cardiology,* vol. 64, Oct. 1, 1989, pp. 725–729.

Kruse et al., "Noturnal Inhibition of Lipolysis in Man by Nicotinic Acid and Derivatives," *Eueopean Journal of Pharmacology,* pp. 11–15.

Grundy, "Cholesterol–Lowering Drugs as Cardioprotective Agents," *The Americn Journal of Cardiology,* vol. 70, Dec. 21, 1992, pp. 271–321.

Head, "Inositol Hexaniacinate: A Safer Alternative to Niacin," *Alternative Medicine Review,* vol. 1, No. 3, 1996, pp. 176–184.

Hoffer, "Vitamin–B–3: Niacin and Its Amide," Internet article obtained Jan. 28, 1997.

METHOD FOR CONTROLLING WEIGHT WITH HYPERICUM PERFORATUM AND GARCINIA CAMBOGIA

BACKGROUND OF THE INVENTION

1. Field of the Invention

This invention relates to a pharmaceutical composition and method of administering the same to a mammal, which pharmaceutical composition acts to control the weight of the mammal. More specifically, the composition acts to at least suppress appetite, and preferably also acts to induce thermogenesis and inhibit lipogenesis, so as to prevent weight gain and/or facilitate weight loss.

2. Discussion of Related Art

Serotonergic neurons control the release of neurotransmitters as a function of food uptake. It is well established that carbohydrate consumption increases serotonin release whereas protein ingestion does not. Biochemically, dietary starch is degraded to sugar which stimulates the pancreas to release insulin. Insulin, in turn, raises the levels of tryptophan in the brain. Tryptophan is a precursor of serotonin, and serotonin affects the mood. Neuronal signaling in food consumption, thus, provides a feedback mechanism to maintain a balance between protein and carbohydrate ingestion. Serotonin, however, also affects several other loci in the central nervous system which control, for example, sleep, pain sensitivity, libido, satiety center, maintenance of optimal blood pressure and mood. See, for example, Wurtman et al., "Brain Serotonin, Carbohydrate-Craving, Obesity and Depression," Obesity Research, Volume 3, Supplement 4, pages 477S–480S (1995). Thus, obese people tend to binge on carbohydrates, which is a common cause of weight gain. People exposed to stress, people in depression and ex-smokers trying to disabuse themselves of nicotine habituation also have a tendency to gain weight. In short, there is a clinical link between serotonin, dietary habits, obesity and depression. See Wurtman et al., supra.

It has been known to use certain anti-depressants as weight control agents. For example, Prozac™ has been known to be used as a weight control agent. However, as well documented, Prozac has several undesirable side effects. It is therefore desired to develop a weight control composition that is free of undesirable side effects.

*Hypericum perforatum*, also known as St. John's wort, has been known to be used in treatments to remedy depression, anxiety, mania, hypochondriasis and fatigue. See, for example, Murray, "The Healing Power of Herbs," $2^{nd}$ Edition, pages 294–301 (1995); Castleman, "The Healing Herbs," pages 321–325 (1991); Harrer et al., "Treatment of Mild/Moderate Depressions With Hypericum," Phytomedicine, Volume 1, pages 3–8 (1994); and De Smet et al., "St. John's wort As An Antidepressant," BMJ London, Aug. 3, 1996. The major active compounds of interest in *Hypericum perforatum* are hypericin and pseudohypericin. *Hypericum perforatum* has the effect of inhibiting serotonin uptake by synaptosomes, thereby increasing the amount of serotonin in the system. This increase in the serotonin level contributes to the anti-depressant activity of *Hypericum perforatum*. See, for example, Perovic et al., "Pharmacological Profile of Hypericum Extract," Drug Research, Volume 45 (II), No. 11, pages 1145–1148 (1995). *Hypericum perforatum* is often reported to have no notable side effects (Harrer et al., supra), or very minor side effects, such as gastrointestinal symptoms, allergic reactions and/or fatigue (De Smet et al., supra), as well as reduced appetite. *Hypericum perforatum* has also been reported to result in an increased appetite (Castleman, supra).

Although *Hypericum perforatum* is known for use as an anti-depressant, it has not been specifically used as an agent for weight control. Serezac™ is a commercially available product containing *Hypericum perforatum*. Serezac is marketed and administered as an anti-depressant.

The majority of commercially available weight control products focus upon only one avenue of weight control, most typically appetite suppression. This avenue seeks to regulate food intake through drug administration directed to one or more systems known to play a role in food digestion. See, for example, Sullivan et al., "Mechanisms of Appetite Modulation By Drugs," Federation Proceedings, Volume 44, No. 1, Part 1, pages 139–144 (1985). Regulation of serotonin level is one such method of appetite suppression.

However, thermogenesis and inhibiting lipogenesis are other avenues of weight control. Thermogenesis is the major mechanism by which the body burns the metabolically active brown fat. Brown fat cells are a part of the sympathetic nervous system, and serve as a locale for the release of norepinephrine, which triggers thermogenesis. Thermogenesis prevents the storage of dietary lipids while also converting stored fat into soluble lipids that are burnt off by the body to generate energy.

Lipogenesis is a process in which excess glucose is converted into fat and stored in adipose tissues throughout the body. Inhibiting this process, for example by binding a material to the enzyme citrate lyase to reduce the production of fat and cholesterol, can act to reduce weight gain and/or induce weight loss.

SUMMARY OF THE INVENTION

It is an object of the present invention to develop a pharmaceutical composition that can effectively act to control the weight of a mammal to which the composition is administered. It is a further object of the present invention to develop a weight control pharmaceutical composition that can act to control the weight of a mammal to which the composition is administered through each of suppressing appetite, inducing thermogenesis and inhibiting lipogenesis. It is a still further object of the present invention to develop a method of administering a pharmaceutical composition to control weight without notable side effects.

These and other objects are achieved by a method of administering a pharmaceutical composition containing *Hypericum perforatum* or the active components thereof to a mammal, preferably a human, in a manner effective to control the weight of the mammal. In the method, the pharmaceutical composition is preferably administered orally. These objects are also achieved by a weight control pharmaceutical composition containing at least *Hypericum perforatum* or the active components thereof, a thermogenic agent and an agent inhibiting lipogenesis, preferably also with a pharmaceutically acceptable carrier.

DETAILED DESCRIPTION OF PREFERRED EMBODIMENTS

The pharmaceutical composition capable of controlling the weight of a mammal to which the composition is administered comprises at least *Hypericum perforatum* or the active components thereof, and also preferably includes a thermogenic agent and/or an agent inhibiting lipogenesis. The pharmaceutical composition also preferably includes a pharmaceutically acceptable carrier.

As mentioned above, *Hypericum perforatum*, also known as St. John's wort, contains both hypericin and pseudohypericin as active components. The composition and method of the invention preferably utilizes an extract of *Hypericum perforatum*. However, rather than an extract, hypericin and/or pseudohypericin may be used alone or together in the composition. Within the system of a mammal such as a human, *Hypericum perforatum* extract, as well as hypericin and pseudohypericin, functions essentially as a monoamine oxidase inhibitor, and, as such, increases the concentration of serotonin in synaptosomes by inhibiting the re-uptake of serotonin in the system. Serotonin release is increased when the mammal intakes carbohydrates. Serotonin thus has a satiety promoting effect in the system which regulates against the over consumption of carbohydrate-rich foods. As such, because *Hypericum perforatum* increases the quantity of serotonin present within synaptosomes, it can act to reduce the desire to consume carbohydrate-rich foods, i.e., it can act to suppress the appetite of the mammal.

A major advantage to the inclusion of *Hypericum perforatum* in a pharmaceutical composition to be administered as a weight controlling agent is that this active compound exhibits no notable side effects. In this respect, *Hypericum perforatum* is desired over other monoamine oxidase inhibitors such as Prozac that has a well documented history of adverse side effects.

According to one embodiment of the invention, a pharmaceutical composition containing *Hypericum perforatum*, preferably also containing a pharmaceutically acceptable carrier, is administered to a mammal in dosages effective to control the weight of the mammal. The weight controlling function of the composition containing *Hypericum perforatum* is believed to occur through appetite suppression as a result of an increase in the serotonin level in synaptosomes.

In another embodiment of the invention, the pharmaceutical composition preferably further contains a thermogenic agent, i.e., an agent inducing thermogenesis. Thermogenesis is the major mechanism by which the body burns metabolically active brown fat. Thermogenesis prevents the storage of dietary lipids and also converts stored fat into soluble lipids that are burnt off by the mammal. As such, a thermogenic agent can act to control and reduce the weight of a mammal to which the composition containing the thermogenic agent is administered.

Any thermogenic agent, or mixture of agents, known in the art may be used. For example, the thermogenic agent may include one or more of kola nut, N-acetyl-L-carnitine, cayenne extract, salicin, niacin or inositol hexanicotinate.

While kola nut is a useful thermogenic agent, it contains caffeine which can cause nervousness and mild agitation so that kola nut is a less desired thermogenic agent, particularly when administered in higher amounts. N-acetyl-L-carnitine is very useful in facilitating the transport of fat into mitochondria for their metabilization to generate energy. Cayenne extract stimulates the production of energy in the form of adenosine triphosphate (ATP) which, in turn, metabolizes more fat. Salicin, which is found naturally in the bark of the white willow, also has been implicated in the stimulation of thermogenesis.

Niacin, also known as vitamin B-3, is known to induce thermogenesis and acts to lower low density lipoprotein (LDL) cholesterol levels and elevate high density lipoprotein (HDL) cholesterol levels. It does so by reducing lipoprotein synthesis in the liver. See, for example, Stone, "Lipid Management: Current Diet Drug Treatment Options," The American Journal of Medicine, Volume 101, Supplement 4A, pages 40S–49S (1996). Niacin, however, can have severe undesirable side effects, the most common of which is a prostaglandin-mediated flush.

A safer form of niacin in terms of reduced side effects is inositol hexanicotinate. Inositol hexanicotinate consists of six (6) molecules of niacin conjugated to one (1) molecule of inositol. The compound is slowly metabolized within the mammalian system to niacin and inositol. Inositol hexanicotinate is thus referred to as a "sustained-release" or "time-release" niacin in that niacin administered in the form of this compound is present within the system over a longer period of time compared to niacin administered alone.

Another form of niacin that might be suitably administered is the so called "no-flush" niacin that is complexed with chromium, and is commercially available.

If niacin, inositol hexanicotinate or other forms thereof are included in the pharmaceutical composition, the composition preferably also further includes a vitamin B-6 compound. The vitamin B-6 compound enhances the effect of the vitamin B-3 compound, i.e., it enhances the thermogenic effect. A most preferred vitamin B-6 compound to use in conjunction with, for example, inositol hexanicotinate, is pyridoxyl phosphate.

The pharmaceutical composition also preferably further includes an agent capable of inhibiting lipogenesis. Lipogenesis is a process in which carbohydrates and excess glucose are converted into fat for storage in adipose tissues throughout the body. Lipogenesis thus results in weight gain. Agents that can inhibit the process of lipogenesis thus can also effectively act to control the weight of a mammal.

The conversion of carbohydrate into fat involves the oxidation of pyruvate to acetyl-CoA. Pyruvate oxidation is an intramitochondrial process while fatty acid synthesis is predominantly an extramitochondrial process. The acetyl group of intramitochondrial acetyl-CoA must therefore be diverted from the intramitochondrial to the extramitochondrial compartment of a cell before it can be converted into fatty acids. This transfer takes place in the form of citrate. Any agent that interferes in this lipogenic process can be suitably added to the pharmaceutical composition.

A most preferred agent for inhibiting lipogenesis is hydroxycitric acid or hydroxy citrate. This material is a powerful inhibitor of ATP:citrate lyase, the enzyme which catalyzes the extramitochondrial cleavage of citrate to acetyl-CoA and oxaloacetate. In other words, hydroxy citric acid inhibits lipogenesis by tightly binding to the enzyme ATP:citrate lyase so as to reduce the production of fat and cholesterol in the system. See, for example, Watson et al., "Citrate and the Conversion of Carbohydrate into Fat," The Journal of Biological Chemistry, Volume 245, No. 22, pages 5993–6002 (1970); Rao et al., "Lipid-Lowering and Anti-obesity Effect of (−)Hydroxycitric Acid," Nutrition Research, Vol. 8, pages 209–212 (1988); Hellerstein et al., "The Indirect Pathway of Hepatic Glycogen Synthesis and Reduction of Food Intake by Metabolic Inhibitors," Life Sciences, Volume 53, pages 1833–1845 (1993); and, Sullivan et al., "Factors Influencing the in vivo and in vitro Rates of Lipogenesis in Rat Liver," J. Nutrition, Volume 101, pages 265–272 (1971).

The enzyme ATP:citrate lyase is important in maintaining the acetyl-CoA pool for fatty acid and cholesterol synthesis. Inhibition of this enzymatic reaction limits the availability of 2-carbon units for fatty acid and cholesterol synthesis. Fatty acid synthesis is thus reduced without altering protein levels. It is believed that hydroxy citric acid reduces food consumption by diverting carbohydrates and fatty acids that would have become fat inside the liver into hepatic glycogen synthesis, which in turn sends a signal to the brain that results in reduced food intake.

Hydroxy citric acid is found naturally in the herb *Garcinia cambogia*, also known as "Malabar Tamarind."

A pharmaceutical composition containing the Hypericum perforatum, the thermogenic agent and an agent inhibiting lipogenesis is believed to control the weight of a mammal to which the composition is administered by simultaneously suppressing the mammal's appetite, inducing thermogenesis and inhibiting lipogenesis in the mammal's system. In this manner, the mammal does not desire to intake further food, existing stored fat is more readily burned off, and new sources of potential fat are prevented from forming fat.

The pharmaceutical compositions according to the invention also preferably include a pharmaceutically acceptable carrier. The pharmaceutical composition preferably takes the form of solid tablets and/or capsules suitable for oral administration, although liquid formulations are also possible. The composition may be prepared into a form suitable for oral administration by any conventional method known to the art.

Any carriers known in the art for oral application compositions may be used. For solid form preparations, such as, for example, powders, tablets, disbursable granules and capsules, a solid carrier may be one or more substances such as diluents, flavoring agents, solubilizers, lubricants, suspending agents, binders, tablet disintegrating agents, encapsulating materials and the like. Suitable carrier materials may include, for example, magnesium carbonate, calcium carbonate, sodium bicarbonate, magnesium stearate, calcium stearate, talc, lactose, sugar, pectin, dextrin, starch, tragacanth, cellulose derivatives, methyl cellulose, sodium carboxymethyl cellulose, a low-melting wax, cocoa butter, alginates, gelatin, polyvinyl pyrrolidone, polyethyl glycols, quaternary ammonium compounds and the like.

Liquid form preparations include solutions, suspensions and emulsions. Suitable carriers may include, for example, water, coloring, flavoring agents, stabilizers and thickening agents. Viscous materials, such as natural synthetic gums, resins, methyl cellulose, sodium carboxymethyl cellulose and other agents known to the pharmaceutical art may also be used.

The composition to be administered may be prepared in accordance with any dose preparation method known in the art, for example mixing, encapsulation, etc., and is not limited. The components of the composition may be added in any order without limitation. The *Hypericum perforatum* is preferably prepared for addition to the composition by, for example, grinding, comminuting, etc. the leaves and forming an extract by any known method, for example an aqueous or organic extract. Preferably, the *Hypericum preforatum* extract is standardized to contain 10% or less hypericin.

Additional materials may also be present in the pharmaceutical composition. For example, the composition may also contain L-phenylalanine, an amino acid that is the precursor of tyrosine which is required for the synthesis of the neurotransmitters epinephrine, norepinephrine and dopamine. L-tyrosine itself may also be present in the pharmaceutical composition.

The pharmaceutical composition may further include tryptophan, or more preferably 5-hydroxy tryptamine (5HT). Tryptophan is a precursor of serotonin. Other conventional materials such as calcium carbonate and magnesium oxide may also optionally be included within the pharmaceutical composition.

One dose of the pharmaceutical composition, for example one tablet or capsule, may contain, for example, 50 to 500 mg, preferably 100 to 250 mg, *Hypericum perforatum* standardized to hypericin. If the composition further contains thermogenic agent(s) and/or agent(s) inhibiting lipogenesis, the composition may contain, for example, 100 to 1,000 mg, preferably 150 to 500 mg, of thermogenic agent(s), and/or 50 to 500 mg, preferably 100 to 250 mg, of agent(s) inhibiting lipogenesis. A single dose of the pharmaceutical composition containing such amounts of active ingredients is most preferably administered in a total amount of two to four tablets per day to the mammal. The total amount of active ingredients within one dose of the pharmaceutical composition may be between, for example, 100 and 1,500 mg, preferably 250 to 1,250 mg, most preferably around 1000 mg.

The total daily amount of *Hypericum perforatum* administered to the mammal may be, for example, 100 to 2,000 mg. The total daily amount of thermogenic agent(s) administered may be, for example, 100 to 2,000 mg. The total daily amount of agent(s) inhibiting lipogenesis administered may be, for example, 100 to 1,000 mg. The composition is preferably administered in spaced dosages throughout the day, for example administered every three to six hours, so as to maintain the level of active ingredients in the system of the mammal. As mentioned above, the doses are preferably administered orally so as to directly introduce the active ingredients into the digestive system of the mammal.

When inositol hexanicotinate is included in the pharmaceutical composition, pyridoxyl phosphate is preferably also included. Such composition is preferably administered in amounts such that the inositol hexanicotinate is administered in a total daily amount of, for example, 250 to 1,000 mg and pyridoxyl phosphate is administered in a total daily amount of 100 to 500 mg.

In a most preferred embodiment, the pharmaceutical composition comprises, for example, *Hypericum perforatum* in an amount of 150 mg, standardized to hypericin, *Garcinia cambogia* (hydroxy citric acid) in an amount of 150 mg, preferably in a from standardized to contain 10% or more hydroxy citric acid, inositol hexanicotinate in an amount of 450 mg (which corresponds to 350 mg basal niacin), pyridoxyl phosphate in an amount of 50 mg, and white willow bark extract (salicin) in an amount of 150 mg for a one dose formulation, for example, one tablet or capsule. This most preferred pharmaceutical composition is preferably administered a total of, for example, two to four times daily.

When the pharmaceutical composition is administered to a mammal, preferably a human, the composition controls the weight of the mammal so that preferably weight gain does not occur and more preferably, weight loss occurs.

What is claimed is:

1. A method of preventing weight gain and facilitating weight loss in a mammal, comprising orally administering to the mammal an amount of a composition effective to prevent weight gain and facilitate weight loss in the mammal, the composition comprising *Hypericum perforatum* or an extract of leaves or flowers thereof containing hypericin, and *Garcinia cambogia* or an extract thereof containing hydroxy citric acid as an agent inhibiting lipogenesis, wherein the composition is administered in an amount such that the total daily amount of *Hypericum perforatum* or an extract of leaves or flowers thereof containing hypericin administered ranges from 100 to 2,000 mg and the total daily amount of *Garcinia cambogia* or an extract thereof containing hydroxy citric acid administered ranges from 100 to 1,000 mg.

2. A method according to claim 1, wherein the composition further comprises a pharmaceutically acceptable carrier.

3. A method according to claim 1, wherein the composition is administered in an amount of two to four single doses per day.

4. A method according to claim 1, wherein the composition is administered in tablet or capsule form, and wherein each tablet or capsule contains a total of between 100 and 1,500 mg of both *Hypericum perforatum* or an extract of leaves or flowers thereof containing hypericin and *Garcinia cambogia* or an extract thereof containing hydroxy citric acid.

5. A method according to claim 1, wherein the composition further comprises inositol hexanicotinate and pyridoxyl phosphate such that the inositol hexanicotinate is administered in a total daily amount of from 250 to 1,000 mg and pyridoxyl phosphate is administered in a total daily amount of from 100 to 500 mg.

6. A method according to claim 1, wherein the composition further comprises at least one thermogenic agent selected from the group consisting of N-acetyl-L-carnitine, cayenne extract, inositol hexanicotinate, niacin and salicin.

7. A method according to claim 6, wherein the composition is administered in an amount such that the total daily amount of thermogenic agent administered ranges from 100 to 2,000 mg.

8. A method of preventing weight gain and facilitating weight loss in a mammal, comprising orally administering to the mammal an amount of a composition effective to prevent weight gain and facilitate weight loss in the mammal, the composition comprising one or both of hypericin and pseudohypericin administered in an amount such that the total daily amount administered ranges from 100 to 2,000 mg, and hydroxy citric acid administered in an amount such that the total daily amount administered ranges from 100 to 1,000 mg.

9. A composition comprising *Hypericum perforatum* or an extract of leaves or flowers thereof containing hypericin, at least one thermogenic agent selected from the group consisting of N-acetyl-L-carnitine, cayenne extract, inositol hexanicotinate, niacin and salicin and *Garcinia cambogia* or an extract thereof containing hydroxy citric acid as an agent inhibiting lipogenesis, wherein the *Hypericum perforatum* or an extract of leaves or flowers thereof containing hypericin is present in an amount of 50 to 500 mg, the at least one thermogenic agent is present in an amount of 100 to 1,000 mg, and the agent inhibiting lipogenesis is present in an amount of 50 to 500 mg.

10. A composition according to claim 9, wherein the salicin is derived from white willow bark extract.

11. A composition according to claim 9, wherein the composition further comprises a pharmaceutically acceptable carrier.

12. A composition according to claim 9, wherein the composition contains inositol hexanicotinate as the thermogenic agent and further comprises pyridoxyl phosphate.

13. A composition according to claim 9, wherein the composition further comprises one or more of 5-hydroxy tryptamine, tryptophan, L-phenylalanine, L-tyrosine, calcium carbonate or magnesium oxide.

14. A composition according to claim 12, wherein the composition further comprises salicin.

15. A composition according to claim 9, wherein the composition is in a form of a tablet or capsule.

16. A composition comprising one or both of hypericin and pseudohypericin in an amount of 50 to 500 mg, at least one thermogenic agent selected from the group consisting of N-acetyl-L-carnitine, cayenne extract, inositol hexanicotinate, niacin and salicin in an amount of 100 to 1,000 mg and hydroxy citric acid in an amount of 50 to 500 mg as an agent inhibiting lipogenesis.

* * * * *